United States Patent [19]
Brill

[11] Patent Number: 5,916,187
[45] Date of Patent: Jun. 29, 1999

[54] DYNAMIC SUPPORT TO CORRECT/PREVENT CARPAL TUNNEL SYNDROME

[76] Inventor: Bonnie E. Brill, 295 Graystone Ter., Suite 1, San Francisco, Calif. 94114

[21] Appl. No.: 08/967,257

[22] Filed: Nov. 6, 1997

Related U.S. Application Data

[63] Continuation of application No. 08/681,529, Jul. 22, 1996, abandoned, which is a continuation-in-part of application No. 08/381,553, Jan. 31, 1995, abandoned.

[51] Int. Cl.⁶ .............................. A61F 5/00; A61F 5/37; A61L 15/00
[52] U.S. Cl. ............................ 602/21; 602/75; 128/879
[58] Field of Search .................... 602/5, 20–22, 602/60, 64, 77; 473/422, 458, 464, 518, 553; 128/877–880

[56] References Cited

U.S. PATENT DOCUMENTS

| | | | |
|---|---|---|---|
| 3,238,939 | 3/1966 | Stubbs | 602/64 |
| 3,327,703 | 6/1967 | Gamm | 128/77 |
| 3,533,407 | 10/1970 | Smith | 602/64 |
| 3,892,239 | 7/1975 | Remiro | 602/63 X |
| 4,193,135 | 3/1980 | Rhee | 2/162 |
| 4,632,105 | 12/1986 | Barlow | 602/64 |
| 4,658,441 | 4/1987 | Smith | 2/910 X |
| 4,701,963 | 10/1987 | Overton | 2/161 A |
| 4,850,341 | 7/1989 | Fabry et al. | 128/44 |
| 4,958,384 | 9/1990 | McCrane | 2/161.6 |
| 4,991,234 | 2/1991 | Greenberg | 602/21 X |
| 5,151,315 | 9/1992 | Ponnet | |
| 5,160,314 | 11/1992 | Peters | 602/21 |
| 5,197,149 | 3/1993 | Overton | 2/162 |
| 5,214,799 | 6/1993 | Fabry | 2/161 R |
| 5,226,190 | 7/1993 | Lynch | 2/19 |
| 5,256,136 | 10/1993 | Sucher | 602/21 |
| 5,413,553 | 5/1995 | Downes | 602/21 |
| 5,478,306 | 12/1995 | Stoner | 602/20 |
| 5,538,501 | 7/1996 | Caswell | 602/64 |

OTHER PUBLICATIONS

Occupational Health & Safety, "Gloves, Behavior Changes Can Reduce Carpal Tunnel Syndrome", J.A. Sebright, pp. 18 & 20, Sep. 1986.

*Primary Examiner*—Richard J. Apley
*Assistant Examiner*—Denise Pothier
*Attorney, Agent, or Firm*—L. E. Carnahan

[57] ABSTRACT

A supportive material and exercise device to correct/prevent Carpal Tunnel Syndrome. The supportive material constitutes an elongated member or strap which may be attached to a glove for retaining the hand in a cupping position so as to reform the Carpal Tunnel area of the hand allowing the natural remodeling of the connective tissue support by approximation support and to strengthen muscles therein. The exercise device, which can be worn interchangeably with the strap or glove, is designed to increase strength in the fingers, thumb and hand, thereby reducing the probability of damage to the Carpal Tunnel area and restoring strength to that area.

17 Claims, 9 Drawing Sheets

DYNAMIC SUPPORT TO CORRECT/ PREVENT CARPAL TUNNEL SYNDROME

RELATED APPLICATION

This is a Continuation of application Ser. No. 08/681,529 filed Jul. 22, 1996, now abandoned which is a Continuation-In-Part of U.S. application Ser. No. 08/381,553, filed Jan. 31, 1995, now abandoned.

BACKGROUND

1. Field of Invention

This invention relates to supportive devices used in medical intervention of human joint problems and exercise apparatus for correction of human joint problems, and more particularly to a supportive material in the form of an elongated strap which may be used alone or on a glove and to an exercise device for Carpal Tunnel Syndrome.

2. Discussion of Prior Art

Carpal Tunnel Syndrome is a well-known, commonly occurring hand condition, sometimes referred to as median compression neuropathy within the carpal canal. The most common symptoms of this condition include intermittent pain and numbness of the hand. Such pain or numbness results from compression of the median nerve, which extends from the wrist centrally into the palm of the hand between the palm heel and the ball of the thumb (thenar). In Carpal Tunnel Syndrome, the median nerve is compressed producing the symptoms of pain or numbness. Treatment of Carpal Tunnel Syndrome varies according to the severity of the condition. Severe conditions usually require hand surgery to sever the transverse carpal ligament, which often results in a weakened hand; albeit, it does relieve the pressure on the median nerve. For less severe cases the use of a splint, which immobilizes the wrist, is sometimes effective. The typical splint provides a cock-up for the wrist and inhibits normal wrist motions. Although there has been some success with this apparatus and anti-inflammatory drugs, there has been a concurrent cost and loss of function.

Carpal Tunnel Syndrome has become such a disabling condition as to cause permanent disability in a portion of the work force. Greatly affected are workers in industries which require repeated manual operations with the hands, such as computer operators, cashiers, typists, workers in meat processing operations, the paper industry, and construction. Carpal Tunnel Syndrome is a leading cause of workman's compensation claims in such industries. Protective gloves have been proposed as one means of preventing Carpal Tunnel Syndrome due to wrist flexion (Occupational Health and Safety September 1986, pp. 18–20). A glove proposed for this purpose, in the foregoing publication, includes a tough pigskin shell wrapped around the wearer's wrist. This glove is heavy, cumbersome, and restricts free action of the wrist. Other prior efforts, such as exemplified by U.S. Pat. No. 4,701,963 issued Oct. 27, 1987 to V. P. Overton, and U.S. Pat. No. 5,214,799 issued Jun. 1, 1993 to J. J. Fabry, are gloves that provide added padding to protect the wrist and hand from vibration and shocks through dampening action. Although impact may be reduced through this pad, it does not aid in structural support of the Carpal Tunnel.

This present invention provides a means that reforms the natural arch found in the Carpal Tunnel and an exercise mechanism to strengthen surrounding weakened musculature. The means includes an elongated member which may be secured to a glove or to just a thumb or finger of the user and wrapped around the hand to form a support for reformation of the Carpal Tunnel in a human hand. The exercise mechanism is a stretch device.

OBJECTIVES AND ADVANTAGES

Several objectives and advantages of the present invention include ease of application, simplicity of operation, self-adjustable compressions to conform to need at a particular point in time, full flexibility of hand and wrist with no loss of function, increase in muscle strength, and minimal medical expense. The dynamic structural support apparatus may consist of a fingerless (or fingered) glove with an adjustable expandable strap, using elastic, and hook and loop adhering materials (such as VELCRO) attached at the posterior area of the glove just below and between the thumb and first finger, as described and claimed in above-referenced application Ser. No. 08/381,553, or it may consist of an elongated adjustable band or strap assembly having a thumb retention means and which is wrapped around the hand to provide the desired stress for Carpal Tunnel reformation. The exercise device may consist of five finger loops attached with extension springs of various sizes or with a resistive (elastic) mechanism consisting of any apparatus that includes holes for the thumb and fingers and that lengthens under stress and returns to its original position.

Further objects and advantages of my invention will become apparent from a consideration of the drawings and ensuing description.

DETAILED DESCRIPTION OF THE INVENTION

The present invention is directed to the correction/prevention of Carpal Tunnel Syndrome, and is carried out via a dynamic supportive material which may be incorporated into a glove or an elongated strap, and and an exercise device constructed of expandable/contractable materials for the correction of human joint problems. Basically the invention involves a Carpal Tunnel strap and an exercise device for the reformation of the Carpal Tunnel of a human hand.

Figure 1:
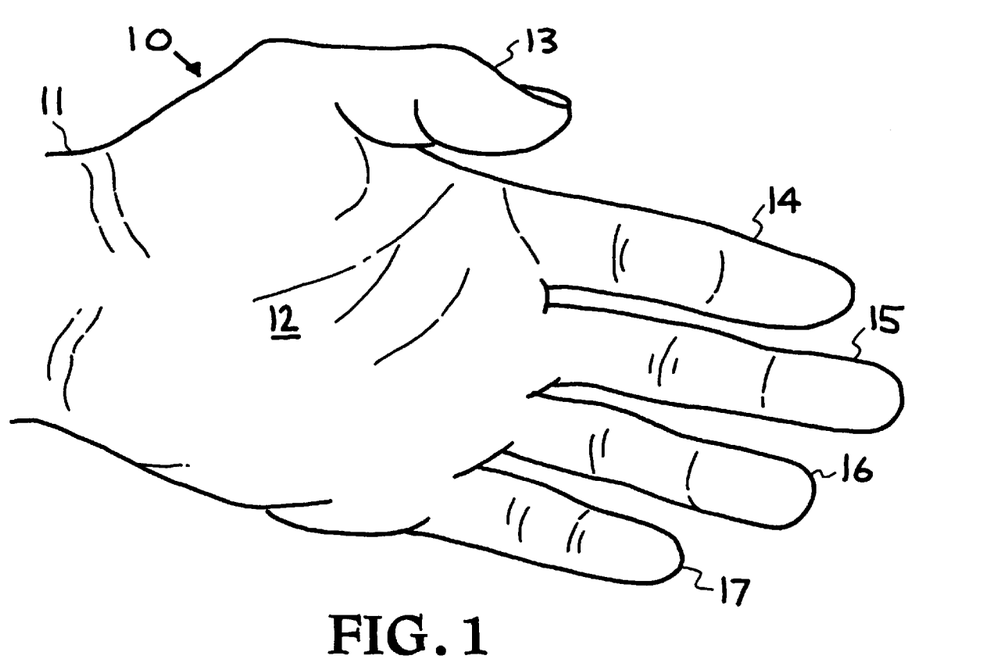
FIGS. 1 and 2 illustrate the palm of a human hand and the Carpal Tunnel thereof.
Figure 2:
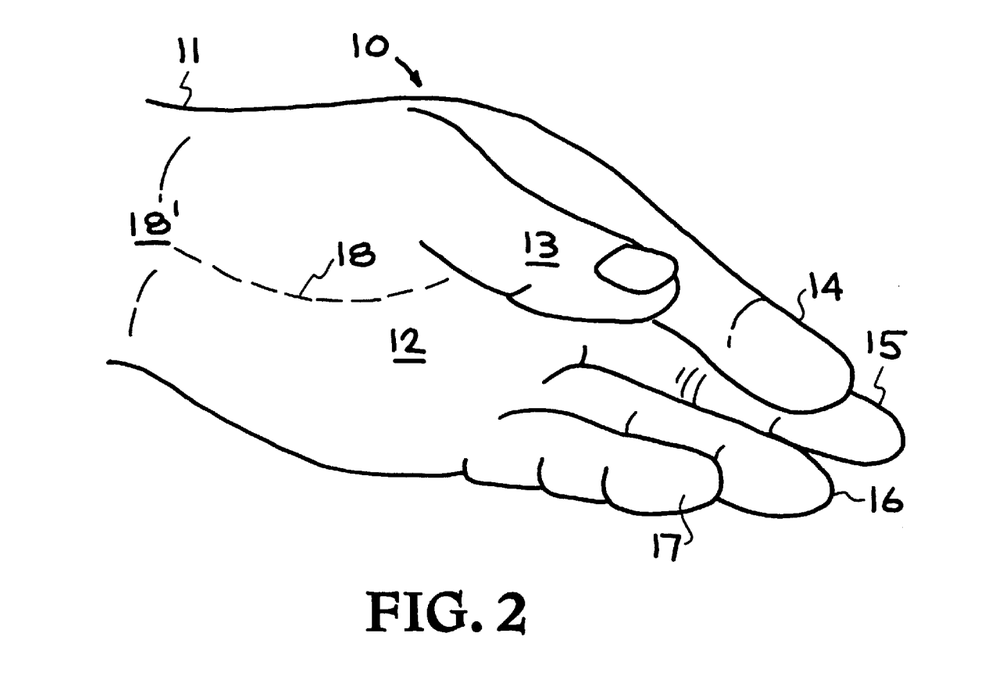

With reference to the drawings, FIGS. 1 and 2 illustrate the palm side of a human hand and the area in which the Carpal Tunnel is formed therein. The hand, generally indicated at 10, connected to a wrist 11, includes a palm side 12, thumb 13, index finger 14, middle finger 15, third finger 16, and little finger 17. FIG. 1 illustrates the hand in an "open" position with the thumb and fingers separated, while FIG. 2 illustrates the hand in a "cupping" position with the thumb and fingers positioned together which forms a line indicated at 18 which extends from an area between the thumb 13 and index finger 14 towards an area indicated at 18', where the hand 10 and the wrist 11 interconnect, which is referred to hereinafter as the Carpal Tunnel area.

Figure 3:
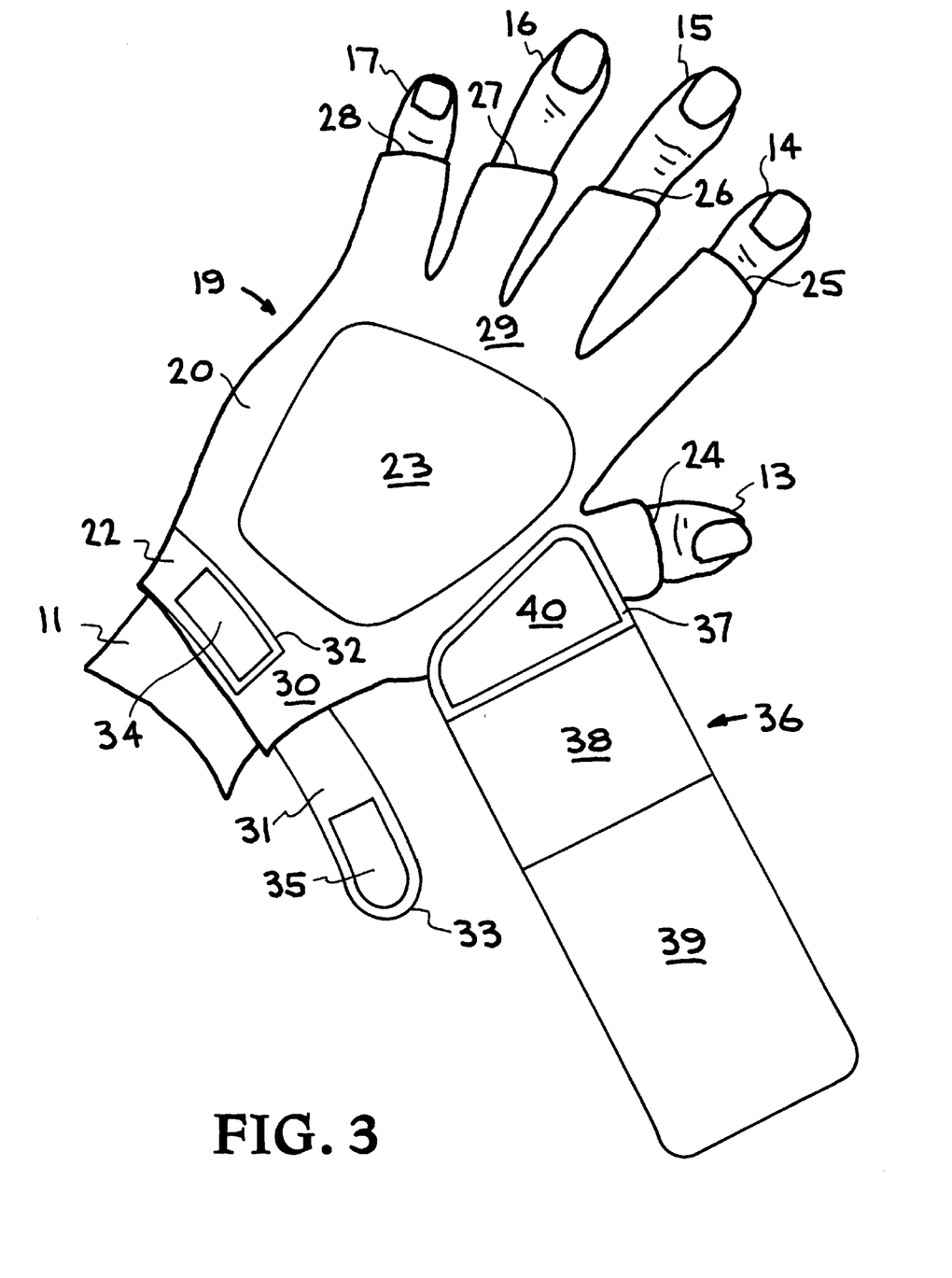
FIG. 3 is a plan view of the back side (dorsal, posterior) surface of a glove showing wrist attachment strap and a Carpal Tunnel strap in an unattached position.
Figure 4:
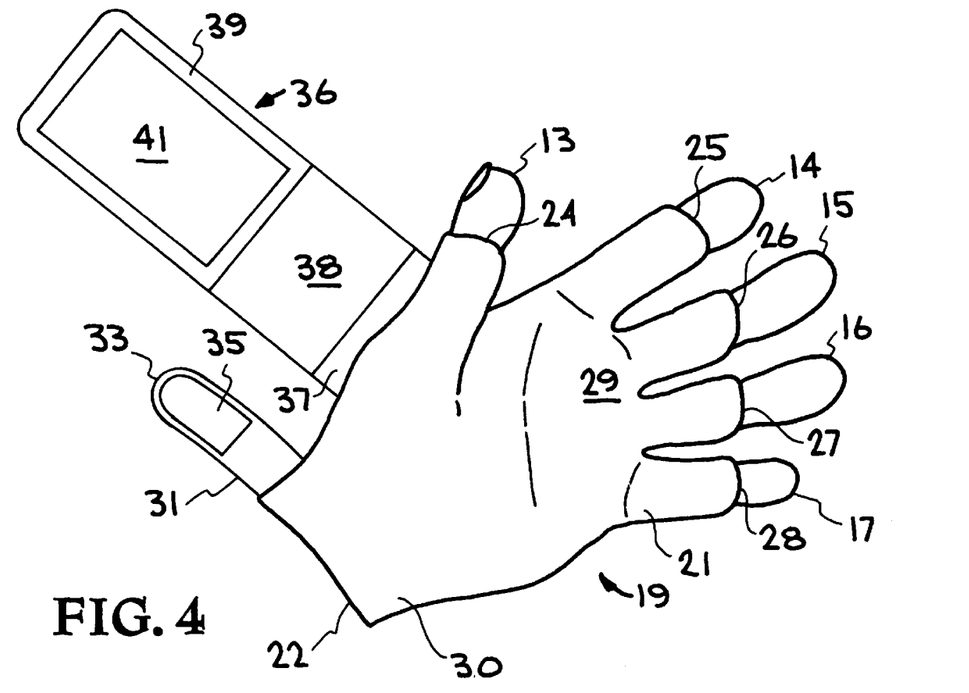
FIG. 4 is a plan view of the palm side of the glove showing both straps in an unattached position.
Figure 5:
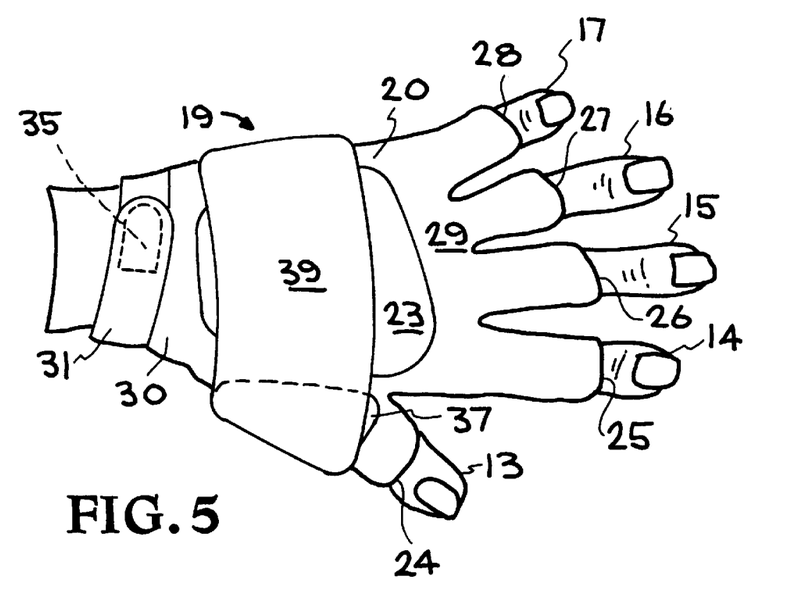
FIG. 5 is a plan view of the back side (dorsal, posterior) surface of the glove showing both straps in a secured position, causing cupping of the hand.

FIGS. 3, 4 and 5 illustrate the dynamic supportive material utilizing a glove generally indicated at 19, which includes a back side 20 (FIGS. 3 and 5), and a palm or front side 21 (FIG. 4). The sides 20 and 21 of glove 19 are stitched or sewn together so as to form an internal hand receiving area, indicated at 22, into which hand 10 is positioned. The back and palm sides of glove 19 may be formed from a single piece of material and/or constructed of various types of material, with the preferred construction being made of leather with a stretchable insert 23 formed in the back side 20, and composed, for example, of a stretchable elastic or nylon-type mesh material. However, the glove can be constructed from a suitable stretchable material provided such material enables the needed support to the hand as discussed thereinafter.

The glove 19 includes a series of thumb and finger openings indicated at 24, 25, 26, 27 and 28, through which thumb 13 and fingers 14–17 extend. A portion or area of the glove 19 adjacent the finger openings 25–28 is referred to as a finger opening base area, indicated at 29. If desired the glove 19 may include full fingers and thumb, or no finger and thumb, instead of half fingers as shown.

Glove 19 also includes a wrist surrounding area or cuff indicated at 30 which includes the internal hand receiving area 22. A wrist strap 31 is attached at a first end 32 to cuff 30 on the back side 20 of glove 19, as seen in FIG. 3, and is adapted to extend around the wrist cuff 30, with a second end 33 being secured to first end 32, as seen in FIG. 5. Wrist strap 31 may be constructed of various material, preferably composed of leather, with end 33 being secured to end 32 via hook and loop pieces or strips, such as VELCRO, indicated at 34 and 35. The first end 32 of wrist strap 31 may be sewed or otherwise secured to the wrist cuff or area 30 on the back side 20 of glove 19. Other types of attaching means, such as a hook and loop arrangement, may be used to adjustably secure end 33 to end 32 of the wrist strap 31. It is to be appreciated that the wrist strap 31 can be adjustably secured to fit various wrist sizes. The wrist strap 31 is located in spaced relation to the expandable and stretchable insert 23 that forms a part of the back side of glove 19. Note that insert 23 extends from adjacent wrist cuff or area 30 toward the finger opening 25–28 and terminates adjacent the finger opening base area 29, and spaced just inwardly of the thumb opening 24, as seen in FIG. 5. This allows the back side 20 of glove 19 to be tightened and gathered about the user's hand to form a very snug and relatively tight fit.

A Carpal Tunnel band or strap, generally indicated at 36, is attached to the back side 20 of glove 19 at an area adjacent the thumb opening 24, as seen in FIG. 3. Band or elongated strap 36 is composed of three sections or portions 37, 38 and 39. Section 37 is attached, such as by sewing or gluing, to the back side 20 of glove 19 adjacent the thumb opening 24 and insert 23, as shown in FIG. 3, and is provided with a VELCRO or hook section 40. Section 38 is composed of an elastic material that covers the palmer surface of hand 10 when section 39, which includes a VELCRO or loop section 41 (see FIG. 4) is secured to section 37, as shown in FIG. 5. By way of example, sections 37 and 39 of elongated strap or band 36 may be constructed of leather, cloth or VELCRO, and elastic section 38 may be made of any stretch material, rubber, or bungie. If hook and loop securing mechanisms are used on sections 37 and 39, they may be interchanged with the loop on section 37 and the hook on section 39.

The Carpal Tunnel band or elongated strap 36 is the portion of the glove 19 that serves to reform the Carpal Tunnel of hand 10, as it moves the hand from the FIG. 1 to FIG. 2 position. By adjusting the band section 39 on section 37, variable forces are promoted for the reformation of the Carpal Tunnel. Strength of adjustments, and thus the amount of tension on elastic section 38 of band 36 is variably controlled by the location relationship and adhesion of sections 37 and 39 of the band. Adjustments are easily implemented by the wearer with the ability to vary stress forces to meet demands made on the Carpal Tunnel during tasks involving the use or the hands. Note that, as shown in FIG. 5, with the bands or straps 31 and 36 in place, the thumb and fingers of the glove wearer are free to move, the mobility thereof depending on the tightness of the band 36 around the hand, and the elasticity of elastic section 38 of the band. While the Carpal Tunnel band or strap 36 has been illustrated and described as having three sections 36–38, with the center section 37 being composed or an elastic material, the entire band or strap may be composed of an expandable/contractable material as described hereinafter with respect to the embodiments of FIGS. 13–19.

Figure 6:
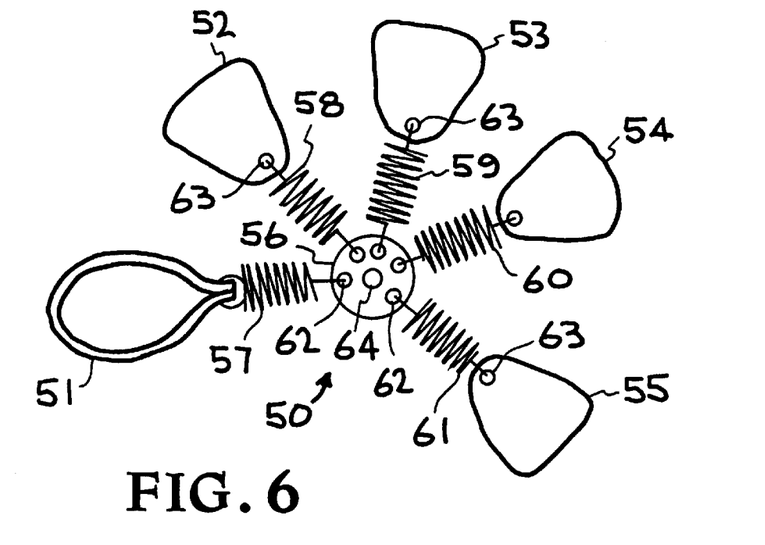
FIG. 6 is a graphic representation of an embodiment of the exercise device with one unit rotated 90°.
Figure 7:
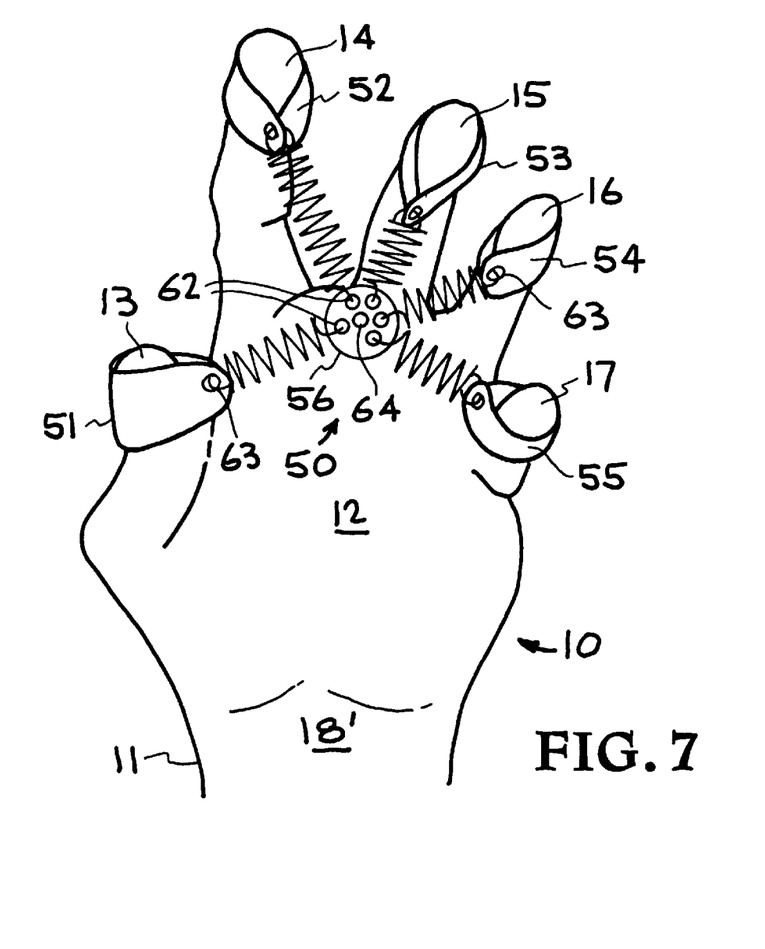
FIG. 7 is a view of the exercise device of FIG. 6 positioned on a hand.

Referring now to FIGS. 6 and 7, an embodiment of an exercise device is generally referenced at 50. This device comprises a thumb retaining means cuff 51, shown rotated 90° in FIG. 6 to illustrate the opening therein, and four (4) finger retaining means or cuffs 52, 53, 54 and 55, with cuffs 51–55 being connected to a central connector or washer 56, via a plurality of expandable/contractable members, such as extension springs 57, 58, 59, 60 and 61. Springs 57–61 are secured in holes or openings 62 in connector 56 and in holes or openings 63 in cuffs 51–55. Note the location of openings 62 in connector 56, which are located to provide the desired pressure on the thumb and fingers. However, the location of openings 62 may not be critical. Springs 57–61 may be replaced by strips of memory retaining expandable/resistive material. Cuffs 51–55 may, for example, be constructed of leather, cloth, plastic, or metal, which is not expandable. Central connector or washer 56 is provided with a central hole 64 by which the device 50 can be hung on a hook during non-use.

As shown in FIG. 7, with the device 50 positioned on the thumb 13 and fingers 14–17 of hand 10, the extensor abductor muscles of the hand are exercised by expansion and contraction of the springs 57–61. This movement of the thumb and fingers strengthens the muscles of hand 10 thus assisting in the rebalancing of muscular strength in the hand. The strength of each of the expandable/contractable members (springs 57–61) differs for each of the thumb and four fingers. The strength of these members will also vary depending on the size of the hand and the hand strength of the wearer.

Figure 8:
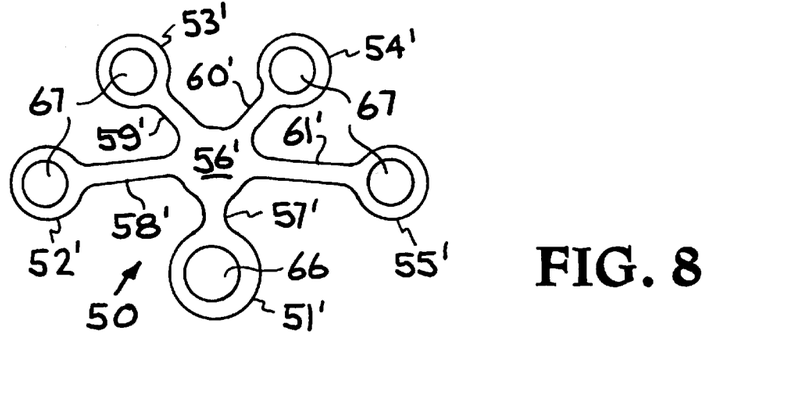
FIG. 8 illustrates another embodiment of an exercise device similar in construction to the FIG. 6 embodiment but utilizing elastic material.

FIG. 8 illustrates another embodiment of an exercise device, which is generally similar in construction to that of FIG. 6 in that it includes a central connector or section from which the expandable/contractable members extend, the difference being that the device is constructed entirely of an expandable/contractable material, thus simplifying the construction and associated fabrication costs. Corresponding components are given corresponding reference numerals. The exercise device of FIG. 8, generally indicated at 50' comprises a single piece of expandable/contractable material having a central or connector section 56', a thumb section 51' having an opening 66, and four (4) finger sections 52', 53', 54' and 55' having openings 67, with the thumb and finger sections being connected to central section 56' by elongated sections 57', 58', 59', 60' and 61'. Note that the location of the elongated sections 57'–61' may be established to provide a desired pressure on the thumb and fingers. Also, the desired pressure can be established by many parameters, including the composition of the expandable/contractable material, the thickness of the material and the width of and/or thickness of the elongated sections. For example, the expandable/contractable material may be composed of latex, silicone, rubber, neophrene, and elastic or elastized cloth, having a thickness of 0.01 cm to 0.2 cm, with the elongated sections having a width of 0.1 cm to 1 cm.

Figure 9:
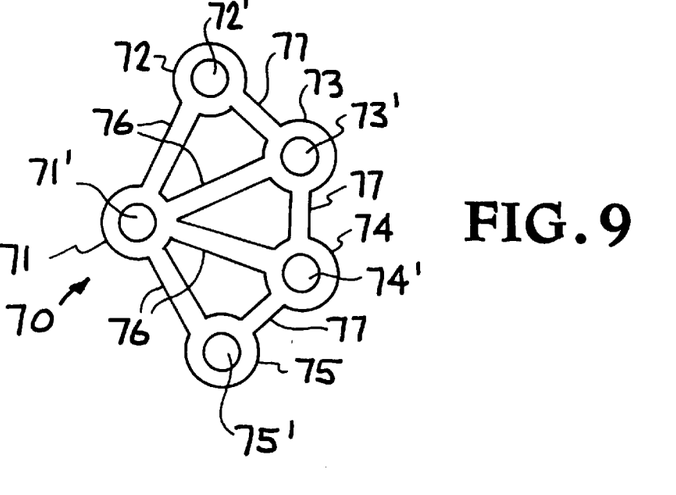
FIGS. 9 and 10 illustrate another embodiment of an exercise device utilizing elastic material but eliminating the central connection as in FIGS. 6 and 8.
Figure 10:
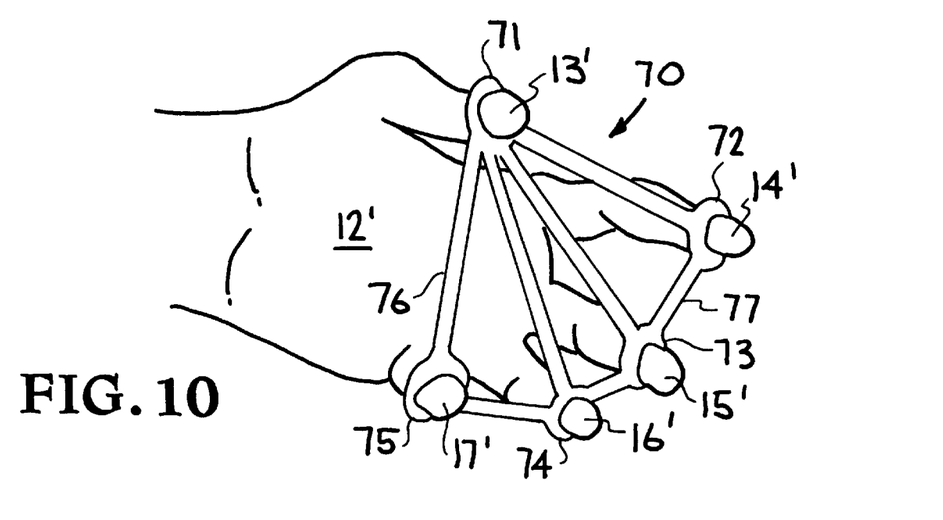

FIGS. 9 and 10 illustrate another embodiment of an exercise device using a single piece of expandable/contractable material, but wherein the central or connector section constitutes the thumb section and wherein the finger sections are interconnected. As shown, the exercise device, generally indicated at 70 comprises a thumb section 71 having an opening 71', finger sections 72, 73, 74 and 75 having respective openings 72', 73', 74', and 75'. The finger sections 72–75 are connected to thumb section 71 by elongated sections 76, with the finger sections being interconnected by elongated sections 77. FIG. 10 illustrates the exercise device of FIG. 9 positioned on a human hand 12' with the thumb 13' and fingers 14', 15', 16' and 17' inserted into their respective openings 71' and 72'–75', whereby the thumb and fingers are exercised by expansion/contraction of device 70. Note that the elongated sections 77 provide stretch between fingers. The device 70 may be constructed of the materials and parameters set forth above with respect to FIG. 8 embodiments.

Figure 11:
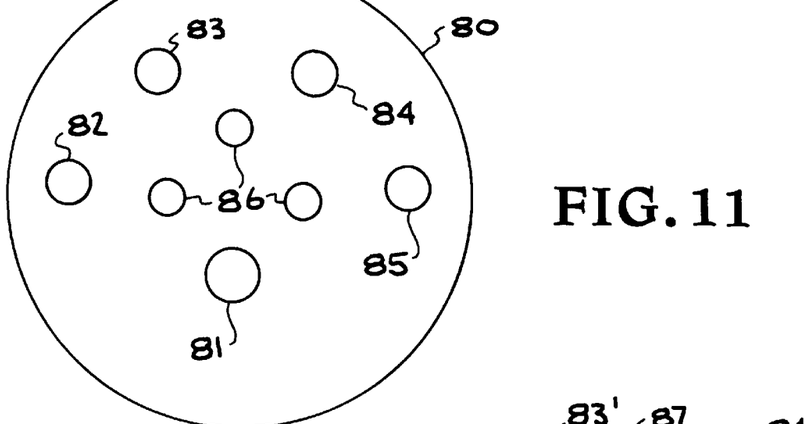
FIGS. 11 and 12 illustrate embodiments of an exercise device composed or a single piece or elastic material with holes for insertion of the thumb and fingers.

FIG. 11 illustrates a simplified embodiment of the expandable/contractable exercise device, which involves a single piece or member of expandable/contractable material or membrane 80 having a thumb hold 81 and finger holes 82, 83, 84 and 85. The location of the finger holes with respect to the thumb hole may be determined by the size of the user's hand, and the pressure on the thumb and fingers determined by several factors including the size of the user's hand, the composition of the material 80, the thickness of the material 80, and the physical condition of the muscles of the hand. Excessive pressure can produce undesired results. The material 80 may be of the same composition and thickness as exemplified above.

Figures 12, 17:
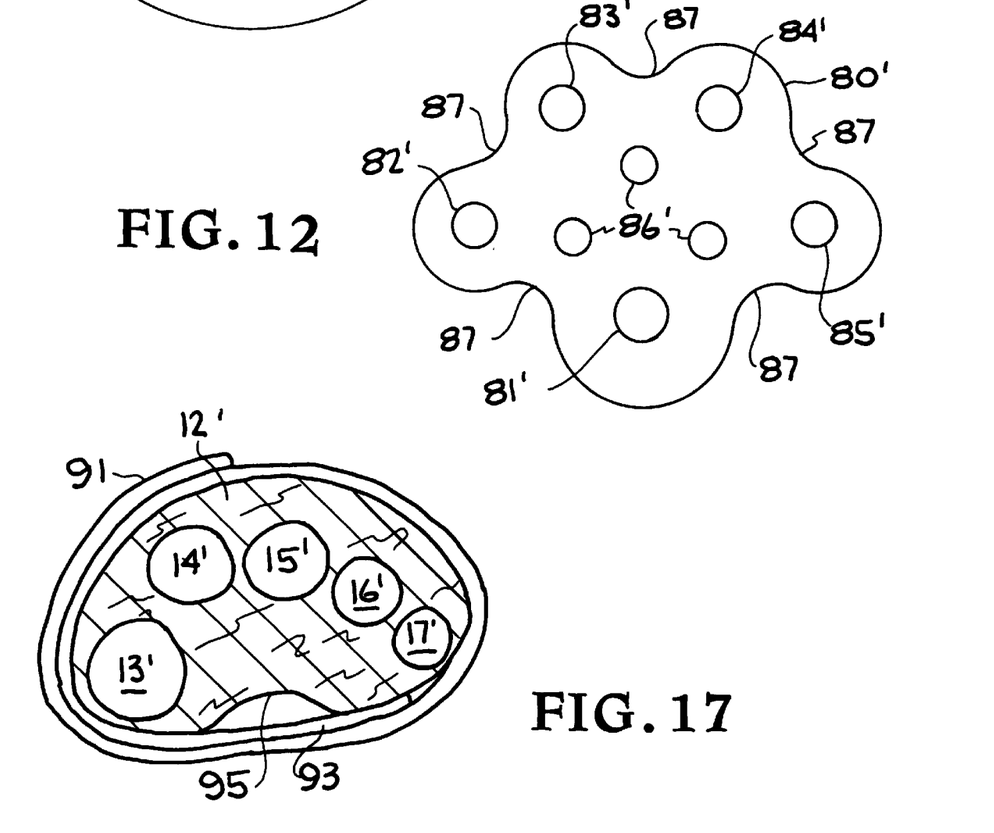
FIGS. 15, 16 and 17 illustrate the strap of FIGS. 13–14 positioned on a human hand.

The FIG. 12 embodiment differs from that of FIG. 11 primarily by the addition of holes in the one-piece expandable/contractable material or membrane which serve to establish the pressure produced by expanding the material, the more holes or the larger size of the holes, the less the pressure on the fingers and thumb when expanding the material. As shown, this embodiment comprises a single member or piece of expandable/contractable material 80' having a thumb hole 81' and finger holes 82', 83', 84' and 85', which may be located with respect to thumb hole 81' as described above. The material 80' is provided with a plurality (four shown) of holes 86, the location and size being determined by the desired expansion pressure of the device. Also, the FIG. 12 device is provided with peripheral scalloped configuration including recessed areas 87 between the adjacent fingers and between the thumb and adjacent finger, which also serves to establish the expansion pressure of the device. The pressure of expansion is again determined by the factors described above, as well as the material composition and parameters exemplified above. A preferred embodiment is constructed of latex, having a thickness of 0.15 cm.

While not illustrated, the embodiments of FIGS. 11 and 12 may include thicker elongated sections intermediate the thumb and fingers and/or between the fingers, which can be formed integral with the one-piece material 80 or 80' during fabrication or can be bonded thereto by conventional procedures.

FIGS. 13–19 are directed to the Carpal Tunnel band or strap, separate from the glove of FIGS. 3–5, since it has been experimentally determined that the band or strap can be utilized effectively without the glove. Tests have shown that by securing the strap to the thumb or finger, the benefits of the strap alone are increased over the strap/glove combination. The embodiments illustrated in FIGS. 13–19 utilize a thumb securing means for the strap rather than a finger securing means, which enables simpler construction and installation, since a finger securing approach requires the securing means to be positioned on the side of the strap rather than at an end thereof, whereby alignment and wrapping of the strap is more effective. Also, tests have been conducted using a strap or band without a securing means, by simply wrapping the strap around the hand. However, slippage and installation/adjustment problems occur without a securing means for the strap.

Figure 13:
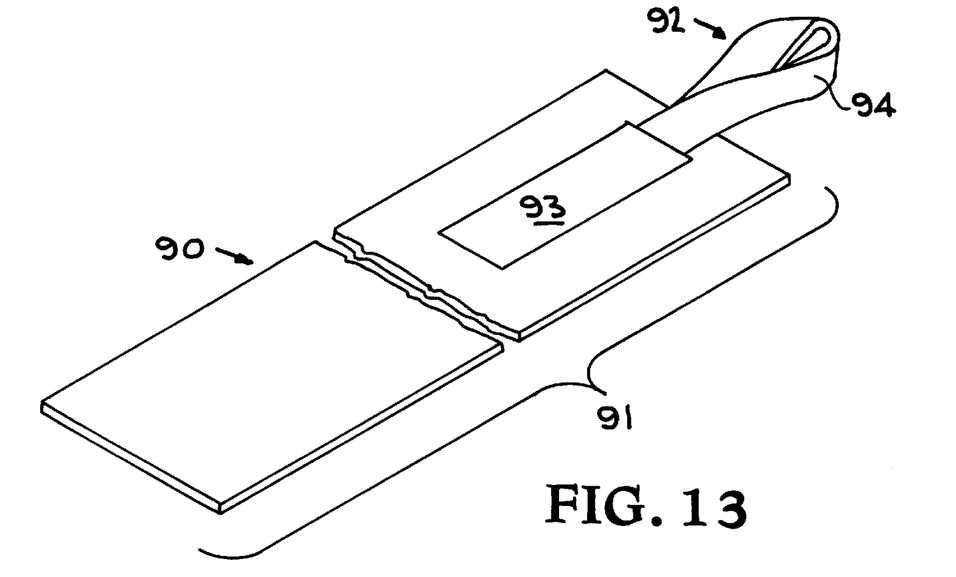
FIGS. 13 and 14 illustrate front and back sides of another embodiment or the dynamic support using the elongated strap but without the glove as in FIGS. 3–5.
Figure 14:
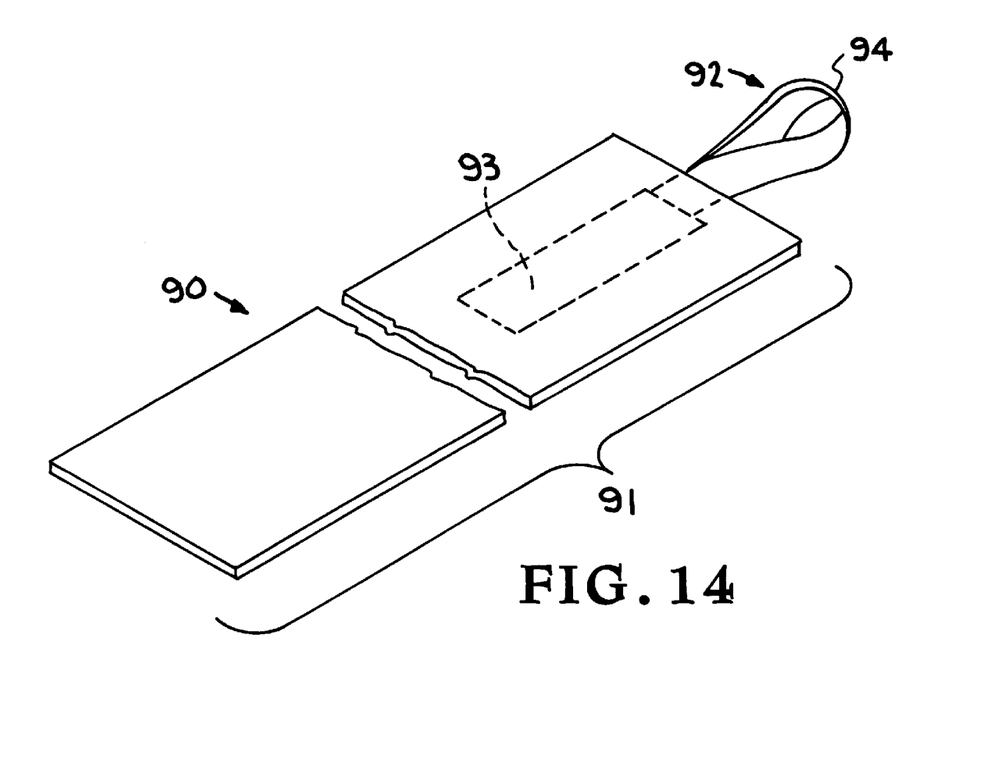

FIGS. 13 and 14 illustrate opposite sides of an embodiment of a Carpal Tunnel band or strap made in accordance with the present invention. The strap generally indicated at 90 comprises an elongated member 91 or support material having a thumb retaining means or member 92 and an adjustment/retention strip or member 93. The support material of the elongated member 91 is expandable/contractable or elastomeric and may, for example, be composed of hook and/or loop with elastic properties or intermittent elastic material without thin adhering means. The elongated member 91 may have a width of ¼ inch to 3 inches and thickness of 0.1 cm to 0.4 cm. Width of the band tends to be based on personal preference. A band width of 1.5–2 inches has had the highest rate of acceptance, based on experiments conducted, with 2 inch preferred because of an increased feeling of security. Actual effectiveness in reformation of Carpal Tunnel was not affected by the 1 inch to 2 inch width variation. The thumb retaining means or member 92 may be secured to member 91 by sewing, bonding, etc., depending on the materials involved, and in this embodiment is composed of a loop 94 of expandable or non-expandable material, such as a hook, loop, pliable plastic cloth, leather, or woven or unwoven material, having a width of 0.5 cm to 2.5 cm and thickness of 0.1 cm to 0.4 cm. Primary thumb loop preference as to expandable vs. non-expandable, width and thickness, based on experiments conducted, appears to be a personal preference with little or no effect on the actual function of the loop. Generally a softer, more pliable material appeared to generate the greatest acceptance. Minimal elasticity was preferred vs. significant elasticity with no significant variation between non-expandable and expandable. Colors seemed to be of greater effect on the user.

Figure 16:
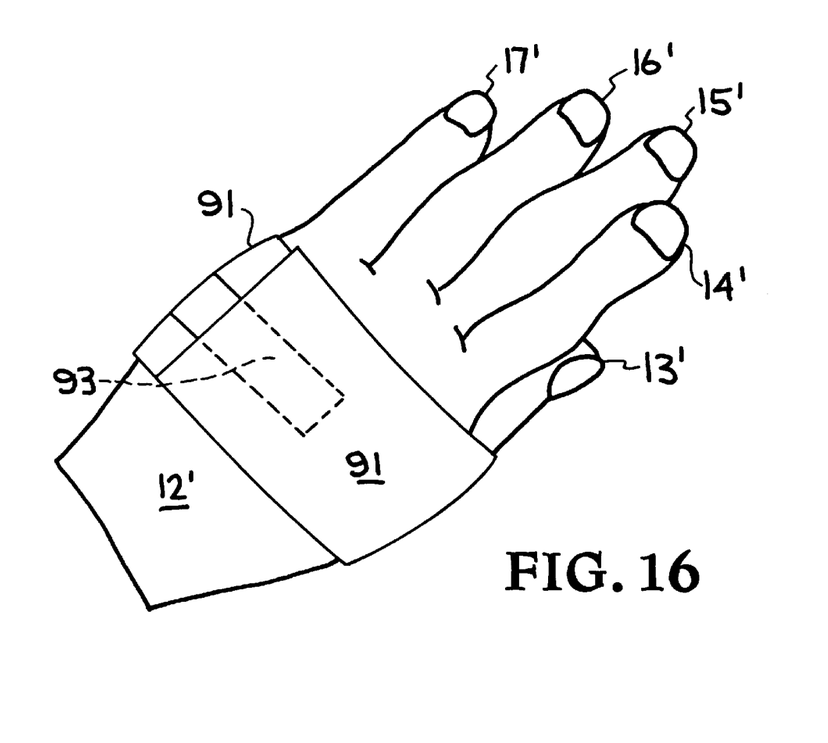

The adjustment/retention strip or member 93 may be composed of loop/hook material, such as VELCRO, sewed or bonded to the member 91, whereby the material of the member 91 can be attached thereto and retained thereby. If desired, a second strip or attachment material may be secured in on an opposite side of the elongated member 91 and positioned so as to contact the strip 93. As seen in FIG. 16, the adjustment/retention member 93 functions to adjustably attach the elongated member 91 after it has been wrapped around a user's hand, as described in greater detail hereinafter.

Figure 15:
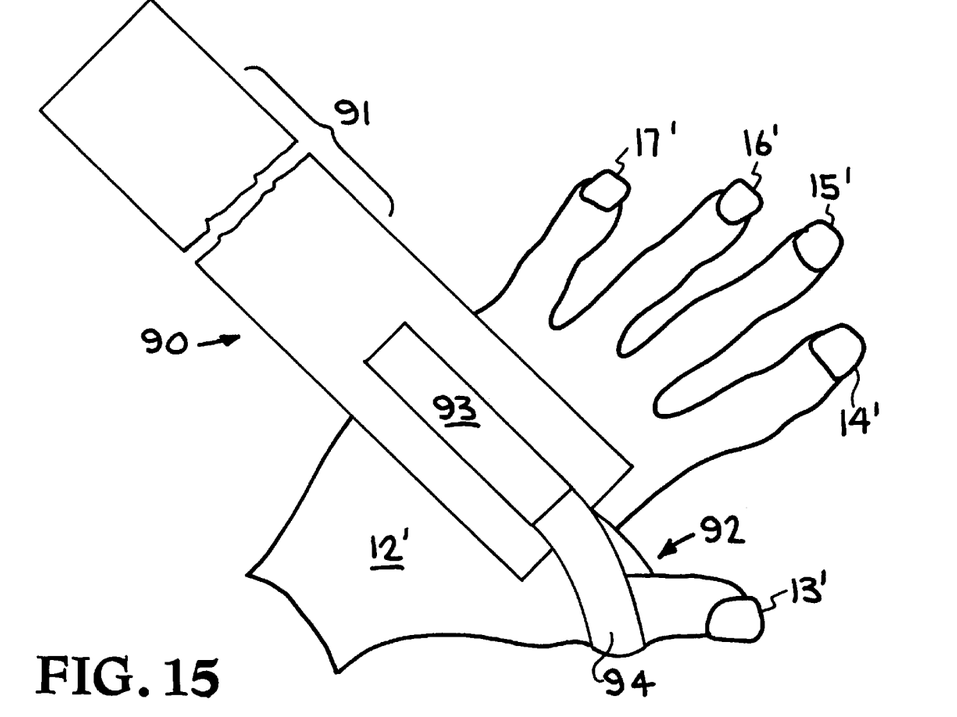

FIGS. 15, 16 and 17 illustrate the Carpal Tunnel strap or band 90 of FIGS. 13 and 14 positioned on a human hand. As illustrated, the loop 94 of the retaining member 91 is positioned over the thumb 13' of a hand 12' and the elongated member extends across the back of the hand 12' and around the hand and is secured by the adjustment/retention strip 93 as seen in FIGS. 15 and 16. However, it can be wrapped in an opposite direction. The strap 90 functions to retain the palmar surface of the hand 12' in a cupped position as shown at 95 in FIG. 17, whereby the Carpal Tunnel area 18' illustrated in FIG. 2 can be reformed while allowing movement of the thumb 13' and fingers 14'–17'. The amount of cupping 95 of the hand 12', as shown in FIG. 17, is determined by the location of the elongated member 90 on adjustment/retention strip 93 of FIGS. 15 and 16, and by the amount of pressure or tightness in application. The cupping 95 can be readily adjusted by the wearer by simply pulling the elongated member 91 from the strip 93 and tightening or loosening the wrap of elongated member 91 around the hand and then wrapping the member 91 over the adjustment strip 93 for securing same to strip 93.

Figure 18:
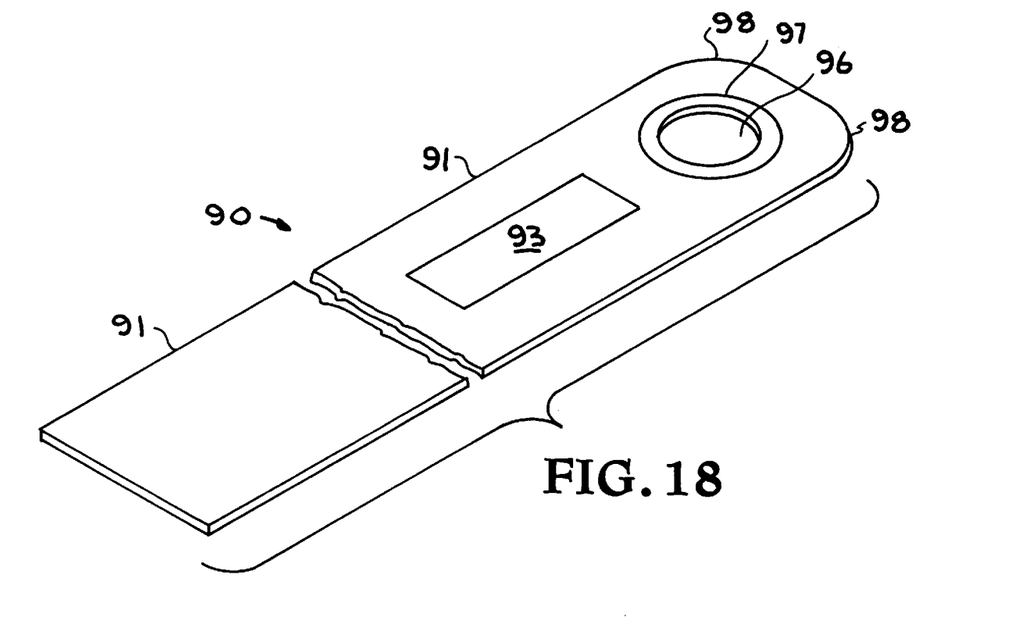
FIGS. 18 and 19 illustrate modifications of the elongated strap arrangement of FIGS. 13 and 14.

FIG. 18 illustrates another embodiment of the Carpal Tunnel band or strap and differs from the FIGS. 13–14 embodiment by elimination of the thumb retaining member 91 and substituting therefor a thumb-hole 96 formed in the elongated member 91'. Depending on the composition of support material of member 91', a reinforcement 97 around hole 96 may be necessary, the reinforcement 97 being composed of stitching or sewing around the hole 96 or by securing another piece of material around the hole 96. Also, the corners or the elongated member 91' adjacent the hole 96 may be rounded as indicated at 98 to reduce rubbing of the end of member 91' on the inner thumb/palm area of the hand.

Figure 19:
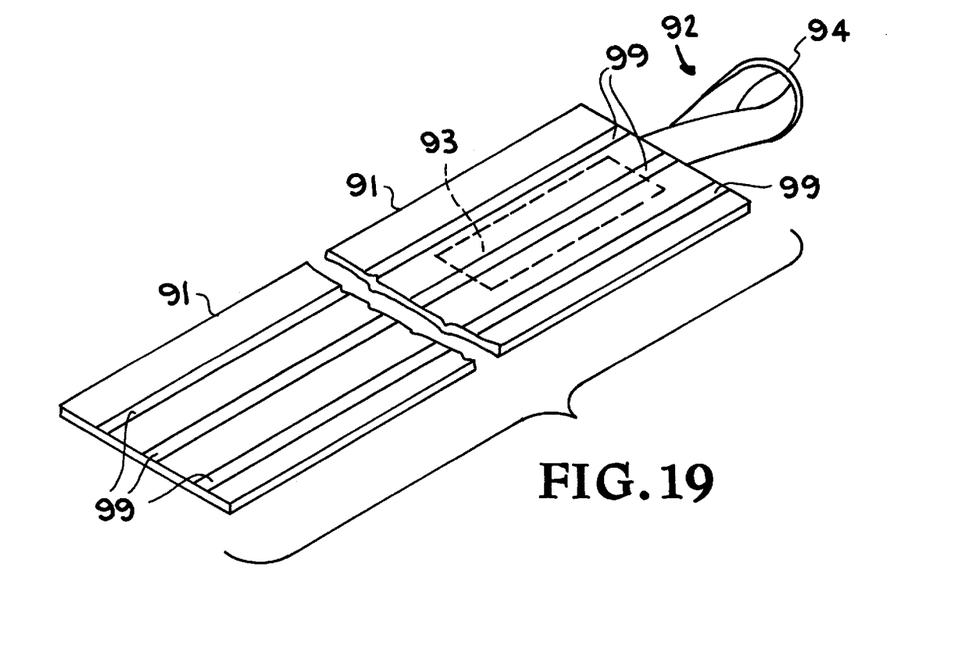

FIG. 19 illustrates a partial embodiment of invention illustrated in FIGS. 13 and 14, but with the addition of slip-prevention strips 99 secured to elongated member 91, on either or both sides thereof, preferably on the side opposite adjustment member 93. The slip-prevention strips 99 may be composed of a non-slip material, such as silicone, latex, rubber, or gum, which is bonded, glued or otherwise secured to elongated member 91. For example, the strips 99 may have a width of 0.01 cm to 0.05 cm and composed of latex or silicone which is secured to member 91 by its self-adhesive properties.

While specific embodiments, materials, etc. have been illustrated and/or described to exemplify and enable a wearer to understand and utilize the invention, such are not intended to be limiting. Modifications and changes may become apparent without departing from the spirit and scope of the invention. It is intended that the scope of the invention be limited only by the scope or the appended claims.

What is claimed is:

1. A device capable of reformation of the Carpal Tunnel in the human hand, consisting of:

a substantially constant width, elongated strap constructed of supportive material including at least a section of elastomeric material and including an adjustment/retention member located intermediate ends of said elongated strap for securing said elongated strap around a human hand by contact between said supportive material and said adjustment/retention member, said elongated strap causes a cupping of the palmer surface of a human hand to provide reformation of the Carpal Tunnel in the human hand;

wherein the cupping of the palmer surface can be increased or decreased by adjustment of the adjustment/retention member along the supportive material of the elongated strap;

said elongated strap including means at one end thereof for securing said elongated strap to only a thumb of a human hand;

said means being selected from the group consisting of an opening located in said one end of said elongated strap and a loop of material attached to the end of said elongated strap; and said elongated strap having a length which only allows one full wrap around the human hand and contact with said adjustment/retention member for securing said elongated strap around the human hand.

2. The device of claim 1, wherein said adjustment/retention member is composed of a loop/hook material.

3. The device of claim 1, wherein said means for securing said elongated strap to only a thumb of a human hand comprises said loop of material attached to the end of said elongated strap, and wherein said loop of material is constructed of material selected from the group of expandable and non-expandable material.

4. The device of claim 3, wherein said loop of material has a width of 0.5 cm to 2.5 cm and a thickness 0.1 cm to 0.4 cm.

5. The device of claim 1, wherein said means for securing said elongated strap to only a thumb of a human hand comprises said opening located in said one end of said elongated strap, and includes reinforcement material around said opening.

6. The device of claim 5, wherein said adjustment/retention member comprises a strip of material secured to said strap.

7. The device of claim 1, wherein the supportive material is entirely elastomeric.

8. The device of claim 1, wherein said supportive material is provided on a surface thereof with material which functions to prevent slipping when positioned on a human hand.

9. The device of claim 1, wherein said elongated strap has a width in the range of ¼ to 3 inches.

10. The device of claim 9, wherein said width of said elongated strap is about 1.5 to 2 inches.

11. The device of claim 1, wherein said elongated strap has a thickness of 0.1–0.4 cm.

12. A method for the reformation of the Carpal Tunnel in the human hand, comprising:

providing an elongated strap constructed of supportive material, providing the elongated strap with an adjustment/retention member for securing the elongated strap around a human hand, providing the elongated strap with means at one end thereof for securing the elongated strap only to a thumb of a human hand, said means being selected from the group consisting of a reinforced opening in an end portion of the elongated strap and a loop of material attached to the end of the elongated strap and securing the elongated strap around a human hand to cause a cupping of the palmer surface of a human hand to provide reformation of the Carpal Tunnel in the human hand.

13. The method of claim 1, wherein securing the elongated member around a human hand is carried out by wrapping the elongated member around the human hand such that no greater than one full wrap around the hand is made.

14. The method of claim 12, additionally including forming the adjustment/retention member of the elongated member from a loop/hook material.

15. The method of claim 14, additionally including adjusting the cupping of the palmer surface of a human hand to increase or decrease the cupping of the palmer surface by adjustment of the supportive material relative to the loop/hook material.

16. A method for reformation of the Carpal Tunnel in the human hand, comprising:

forming an elongated member of supportive material, providing the elongated member with means at one end for securing said elongated member only to a thumb of a human hand selected from the group consisting of an opening in the elongated member and a loop of material secured to the elongated member, providing the elongated member with an adjustable/retention means, positioning the means for securing the elongated member over a thumb of a human hand, wrapping the elongated member around the human hand not greater than one full wrap to cause a cupping action of the palmer surface of a human hand to provide reformation of the Carpal Tunnel in the human hand; and securing the elongated member around the hand with the adjustable/retention means.

17. The method of claim 16, additionally including providing the elongated member with at least a section containing elastomeric material.

* * * * *